United States Patent [19]

Tammisalo et al.

[11] Patent Number: 5,386,448
[45] Date of Patent: Jan. 31, 1995

[54] METHOD FOR IMAGING AN OBJECT BY MEANS OF A PANORAMIC APPARATUS EQUIPPED WITH EXPOSURE AUTOMATICS

[75] Inventors: Erkki Tammisalo, Turku; Tuomas Kyllönen, Espoo, both of Finland

[73] Assignee: Orion-Yhtyma Oy, Helsinki, Finland

[21] Appl. No.: 72,917

[22] Filed: Jun. 7, 1993

[30] Foreign Application Priority Data

Jun. 12, 1992 [FI] Finland .................................. 922733

[51] Int. Cl.⁶ .............................................. H05G 1/44
[52] U.S. Cl. ................................ 378/38; 378/97; 378/108
[58] Field of Search ............. 378/38, 39, 40, 96, 378/97, 108, 146, 110, 112

[56] References Cited

U.S. PATENT DOCUMENTS

| | | | |
|---|---|---|---|
| 3,932,756 | 1/1976 | Cowell et al. | 250/361 |
| 4,021,672 | 5/1977 | Franke | 378/97 X |
| 4,035,650 | 7/1977 | Franke | 378/97 |
| 4,813,060 | 3/1989 | Heubeck et al. | 378/39 |
| 4,815,115 | 3/1989 | Nieminen et al. | 378/38 |
| 4,953,189 | 8/1990 | Wang | 378/108 |

FOREIGN PATENT DOCUMENTS

| | | | |
|---|---|---|---|
| 0125349 | 11/1984 | European Pat. Off. | H05G 1/44 |
| 0358828 | 3/1990 | European Pat. Off. | G21K 1/04 |
| 0432119 | 6/1991 | European Pat. Off. | A61B 6/00 |
| 4222941 | 2/1993 | Germany | H05G 1/44 |

*Primary Examiner*—David P. Porta
*Attorney, Agent, or Firm*—Dressler, Goldsmith, Shore & Milnamow, Ltd.

[57] ABSTRACT

The invention relates to a method for imaging a desired object by using a panoramic X-ray radiography apparatus equipped with exposure automatics, the apparatus including an X-ray generator (5), an X-ray tube (6), and an image receptor (8) with its holder (10). The detecting of the cone of rays (7) which has passed through the object, for the purpose of determining the exposure value, is carried out during the imaging at points positioned in each given case at different heights (17) in the cone of rays, by using one or more detectors (1). The positioning can be done either by moving the detector or by activating a certain detector in an arrangement of a number of detectors.

16 Claims, 2 Drawing Sheets

METHOD FOR IMAGING AN OBJECT BY MEANS OF A PANORAMIC APPARATUS EQUIPPED WITH EXPOSURE AUTOMATICS

The invention relates to a method for imaging an object by means of a panoramic X-ray photography apparatus equipped with exposure automatics, the apparatus including an X-ray generator, an X-ray tube, and an image receptor with its holder.

It is known, as evidenced by publication DE-2 650 872, to place the radiation detector of exposure automatics between the object to be imaged and the film and to perform the detecting and control of the radiation dose as a continuous process throughout the imaging. This requires expensive detectors of a special construction, e.g. ionization chambers, in order that the detectors should not be visible in the image. It is also known to use inexpensive radiation-absorbing detectors and to place them behind the film receptor, as described in Finnish patent application 850415, or between the film and the object, either in front of or beside the cone of X-rays, in which case the measuring and control of the radiation level are carried out before the imaging, by means of separate exposure directly from the cone of rays or from a field of rays deflected from the cone of rays, as defined in patent FI-76234.

Although a number of methods have been proposed for implementing the exposure automatics in panoramic apparatuses, panoramic apparatuses are in general not equipped with exposure automatics. This is due to the fact that exposure in imaging carried out using exposure automatics does not on average succeed more often that does imaging carried out by using manual control. Also, the known exposure automatics are not suitable for imaging using present-day panoramic apparatuses in which only the maxilla or the mandible, or parts of them, is exposed.

The size and shape of the jaws vary from one patient to another. The positioning of the patient, which in panoramic imaging is done by tilting the head, resting on the tip of the mandible or on the front teeth, and by adjusting the position of the jaws relative to the layer being imaged in the front-back direction, will affect the position of the jaws in bomb the vertical and the horizontal direction. Differences in patient size and positioning in imaging are indeed reflected most drastically in the back part of the mandible, i.e. in the area of the ascending ramus, which is the first jaw structure coming into the cone of rays, and from which the detecting can in practice be started. When there appear great variations in the position of the ascending ramus relative to the image field, fixedly positioned detectors do not necessarily strike the object to be measured, i.e. the area of the ascending ramus. Furthermore, in the area of the ascending ramus, various surrounding structures are often projected, such as the soft palate, the base of the tongue, the opposite mandibular angle, the air space of the pharynx, or the air gap between the base of the tongue and the palate. Since these structures run almost horizontally in the area of the ascending ramus, a fixedly positioned detector may run through a measuring cycle in the above-mentioned structures, and thus the measuring result will be distorted and not correspond to the density of the bone. If, on the other hand, the detecting is carried out or continued at a later stage of the imaging, metal fillings and crowns of the teeth, or their metallic artificial roots, i.e. implants, will complicate detecting.

It is an object of the method according to the invention to develop the technology used for determining the automatic exposure level in panoramic X-ray radiography apparatuses so that the success percentage achieved by using exposure automatics will be better than that achieved by manual control.

According to the invention, this object is achieved by not starting the detecting for determining the exposure level until the time when the detector strikes the target area, i.e. the back edge of the ascending ramus, and by positioning the detector, i.e. by moving the detector or by activating certain detectors downwards during the detection, at a velocity which gives the detector a direction of movement corresponding to the angle of tilt of the ascending ramus, in accordance with the characterizing clause of claim 1.

It can be deemed to be the most important advantage of the invention that the detecting takes place in a controlled manner in the area of the ascending ramus even when the size and shade of the jaws of the patient and the imaging position vary. Furthermore, owing to the downwardly oblique movement, the detection point will shift in a direction transverse to the surrounding structures becoming imaged in the area of the ascending ramus, whereby their interfering effect is reduced. When the detector is moved or activated at a speed sufficient for its positioning, it is also possible to use radiation-absorbing detectors, since the X-ray shadow created by them is reduced by the movement to such an extent that it is not distinguishable in the image to the naked eye.

The invention is described below in detail, with reference to the accompanying drawings, which detect certain embodiments of the apparatus used for carrying out the method according to the invention.

Figure 1:
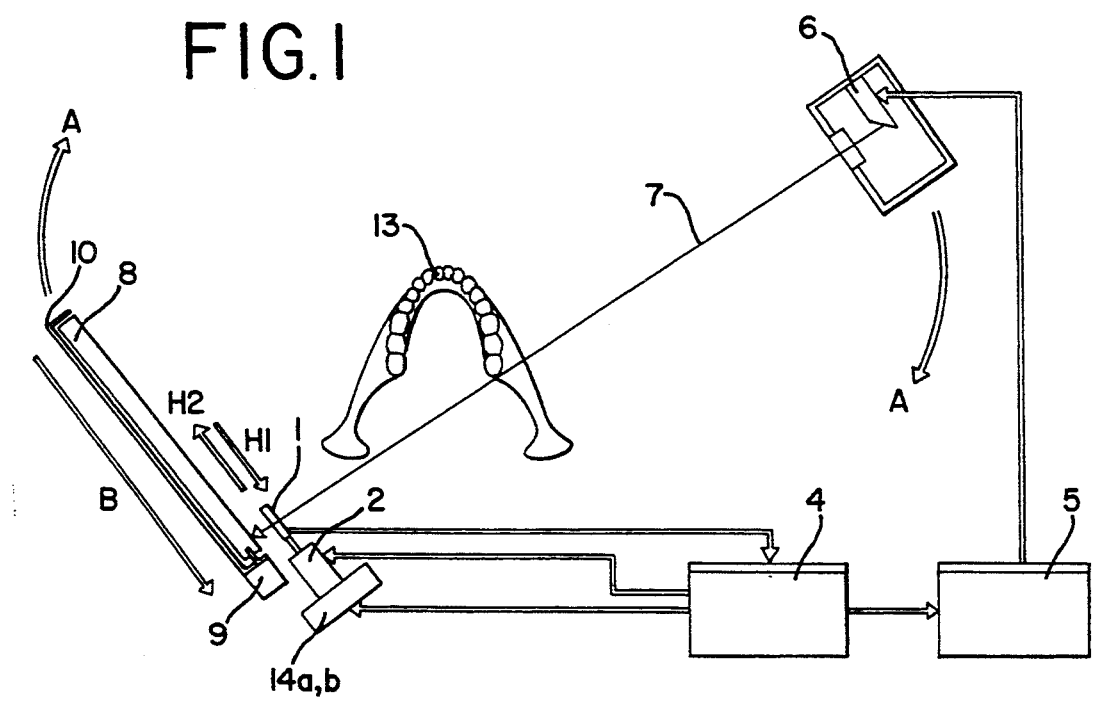
FIG. 1 depicts a block diagram of the first embodiment of the apparatus for carrying out the method of the invention, and a diagrammatic top view of the apparatus.

Since panoramic X-ray photography methods and apparatuses are per se commonly known and used, they are not described in greater detail in this context.

The most important parts of a panoramic apparatus include an X-ray generator 5, an X-ray tube 6, from which, during exposure, a narrow vertical 15 beam of rays 7 is directed through the object 13 onto the image receptor 8. The image receptor 8 and the X-ray tube 6 are interconnected by a common arm structure, not shown in the drawing. During imaging, the X-ray tube 6 and the image receptor 8 turn, on the rotational bearing on the arm, around the object 13 being imaged, in the direction of arrow A. Simultaneously the transfer frame 10 moves the image receptor 8 in the direction of arrow B. The frame 10 which supports and moves the image receptor is equipped with means 9 sensing the sensitivity of the image receptor. The image receptor 8 may be a film, a stimulable memory plate, a CCD cell, or any other image-recording element known per se.

For certain receptor types a movement of the receptor relative to the cone of rays is not required; a shifting activation of the area concerned at each given time will suffice.

The exposure automatics according to the invention comprise, in the embodiment of FIG. 1, a detector 1 which measures radiation and transfer devices 2 and respectively 14a, b which move the detector mechanically in both the horizontal and the vertical direction. The embodiment of FIG. 2 comprises, in addition to the detector 1 and its transfer devices 2 and 14a, b, also a second detector 11 and a mechanical transfer device 3 which moves it in the horizontal direction. In this representation, detector 11 is in alignment with the detector 1, and thus they are not distinguishable from each other. The transfer devices 2 and 14a, b are depicted here by dashed lines. Both detectors are connected to a control unit 4, which in turn is connected to control the transfer devices 2, 3 and 14, as well as the X-ray generator 5.

The transfer devices and the detectors can best be placed on the front side of the secondary shutter. The secondary shutter is a metal plate located on the front side of the image receptor —thus, on the side of the patient—and having a vertical slit of approx. 6–8 mm, through which a cone of rays 7 of approximately the same width will travel and expose the receptor 8. The purpose of the horizontal movement is to transfer the detector from beside the slit to the area of the slit itself so that the cone of rays will not strike the detector when irradiation begins. The length of the movement is approx. 10 mm. The secondary shutter has not been drawn in the figures.

The horizontal movement of the detector 1 or the detector arrangement 20 may be effected by means of, for example, an electromagnet, and the vertical movement by means of, for example, a step motor. The detector 1 or the detector arrangement 20 is moved into the cone of rays by a horizontal transfer simultaneously with the starting of imaging. Before the rays are turned on, the rotating mechanism and the arm structure, as well as the cassette 10, must reach a certain velocity and position. During this short period of time also the position of the detector 1 or the detector arrangement 20 is shifted from beside the secondary shutter to the area of the slit in it, at which the cone of rays which has penetrated the patient's head is aimed.

Figure 3:
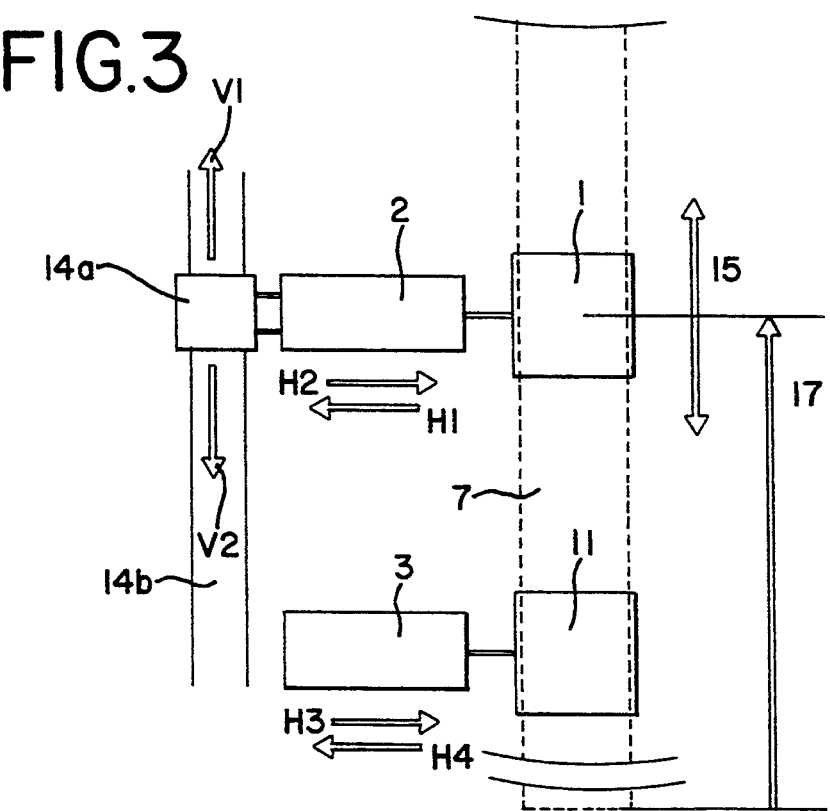
FIG. 3 depicts a detail of the apparatus of FIG. 2, as seen in the direction of the X-ray beam.

FIG. 3 shows both detectors 1 and 11 as seen in the direction of radiation of the cone of rays 7. The cross sectional shape of the cone of rays 7 is depicted by dashed lines, the location of the detectors 1, 11 one on top of the other in the cone of rays 7 being thus observable, as well as the vertical movements V1, V2 of the detector 1 transfer devices and the horizontal movements H1, H2 of the detector, as well as the horizontal movements H3, H4 of the detector 11.

In the event that the detector 1 or 21 is sufficiently transparent to X-rays, i.e. it will not leave a shadow hampering the interpretation of the image, the said horizontal movement is unnecessary.

In the embodiment of FIG. 1, when the imaging program has been selected, the detector transfer device 14a, b, controlled by the control unit, will move the detector 1 in the vertical direction 15 to a position 17 (FIG. 3) which is most optimal for the detecting function to be performed. This optimal position 17 in the vertical direction 15 can be determined on the basis of previous imagings of a large number of patients. After the imaging has started, the detector transfer device 2, controlled by the control unit 4, will transfer the detector 1 in a horizontal direction into the cone of rays 7. The initial detecting of radiation by using the detector 1 will start immediately as the X-radiation is turned on and as the detector is in the slit of the secondary shutter. The purpose of the initial detection is to find the point at which the detecting which determines the actual final exposure values (mAs) is to be started.

When the image receptor 8 has, after the above-mentioned starting, traveled over a predetermined distance or when the dose intensity of the radiation decreases strongly, as for example when the cone of rays 7 strikes the object being imaged, i.e. in the area of the ascending ramus of the mandible, the detecting which measures the exposure level will start and at the same time the transfer device 14a, b will begin to move the detector 1 or the control device 16 will activate the corresponding detectors 21 in the cone of rays upwards or downwards at the velocity and over the distance 17 set by the preprogrammed control unit 4. The said point reducing the dose intensity is thus the back edge of the ascending ramus of the mandible, where the dose intensity of the radiation arriving at the detector drops to 1/5 or lower. In those cases (5–10%) in which the shadow of the patient's cervical spine will come all the way to the back edge of the ascending ramus, the said change in the dose intensity is not produced. For this reason, if the said threshold is not "found", the detection determining the exposure level will start automatically after the film has traveled preferably over a distance of approx. 35–40 mm. In case the receptor 8 is of the type which need not be mechanically moved in a horizontal direction, the detection is started at a point corresponding to this distance in the imaging sequence or within the portion of imaging distance B. In panoramic radiography the detector i is moved, for example, downwards, or in the detector arrangement 20 described below, the detector 21 at this distance is activated or detectors 21 are activated in direction V2 approx. 35–40 mm after the dose intensity has been observed to have dropped strongly or when the image receptor has moved in direction B over at least approx. 30 mm. Thereafter the control unit 4, by mediation of the transfer device 2, will remove the detector 1 from the cone of rays and will compare the value obtained from the detector 1 or 21, proportional to the radiation intensity, to the empirically sought, for example 10-step, exposure level scale, and will select from the scale the step closest to the value at which the film will be exposed correctly. More precisely, this can be done, for example, so that when the detection point moves downwards over, for example, a distance of 35 mm, the mean of the measurements over the distance of the first 20 mm is read and the first adjustment of the exposure level is carried out according to the said value, and then the mean of measurements over the distance of the last 15–20 mm is read and the final adjustment of the exposure level is carried out on the basis of a calculated value in which the latter measurement has, for example, double the weight of the first measurement, since the latter measurement takes place in an area in which interfering shadows are not cast by the surrounding tissues. The control unit 4 will always select the imaging voltage coming to the X-ray tube so that the contrast in the image will be most advantageous in terms of diagnostic information. Only if the other imaging parameters, such as the sensitivity of the image receptor, the anode flow, or the exposure time, will not allow the selection of the imaging voltage most advantageous in terms of diagnostic information, the control unit 4 will increase the voltage.

When the exposure level is determined in the area of the ascending ramus and not immediately at the beginning of the imaging, the area of the temporomandibular joint, important in, for example, diagnostics, may be under- or overexposed. For this reason, in the first embodiment of the method the initial exposure level is determined by manual control. This is done simply by selecting at the size selection unit 12, for example, one of the following patient sizes: 1) very small; 2) small; 3) medium-sized; 4) large; and 5) very large. On the basis of the patient size selection the control unit 4 will, taking into account the sensitivity of the image detector 8 used, automatically set for the selected patient size the empirically sought exposure values which will give the image the correct darkness and as good a contrast as possible. If patient selection is not carried out, the control unit 4 will adjust the exposure values so as to correspond to a medium-sized patient.

Figure 2:
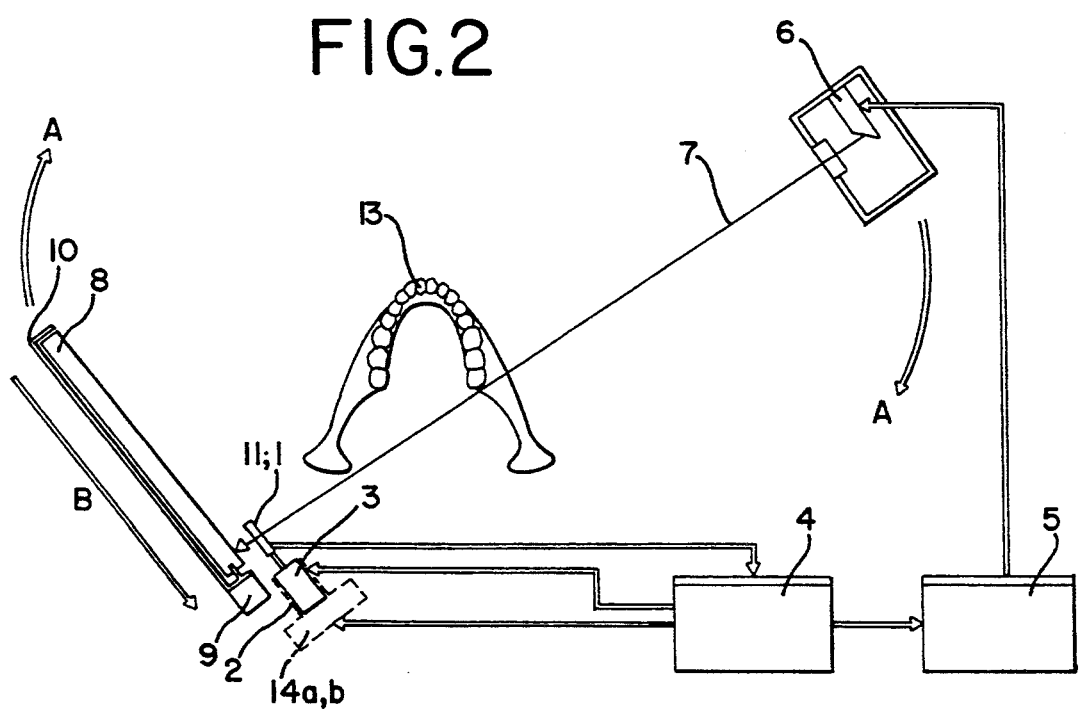
FIG. 2 depicts a block diagram of a second embodiment of the apparatus for carrying out the method of the invention, and a similar diagrammatic representation of the apparatus as shown in FIG. 1.

The embodiment of FIG. 2 differs from the embodiment of FIG. 1 in that the initial exposure level is determined by detection carried out using another, separate detector 11. In this embodiment the detector transfer device 3, controlled by the control unit 4, transfers the detector 11, which has been placed at the lower edge of the image receptor 8, into the cone of rays 7 as the imaging has started. Detecting starts at the same time, and it will continue until the image receptor has traveled over a distance of about 15 mm in direction B. On the basis of the information obtained from the detection, the control unit will select, as described in connection with the first embodiment, out of the empirically sought exposure levels corresponding to five different patient sizes the one which is closest to the level determined by the detection. Simultaneously with the measuring carried out by using the detector 11 of the initial exposure level, there also starts detection carried out by detector 1, which is carried out in accordance with what has been described regarding the first embodiment 1.

FIG. 3, which depicts a detail of the first and second embodiments, shows the transfer devices 2 and 14 of the detector 1. The transfer device 2, which is driven by, for example an electromagnet, is structurally similar to the transfer device 3. The transfer device 3 is, however, fixedly positioned, whereas the transfer device 2 has been attached to transfer devices 14a, b, which are moved in the direction of the vertical axis 15 of the cone of rays, for example by a step motor.

Figure 4:
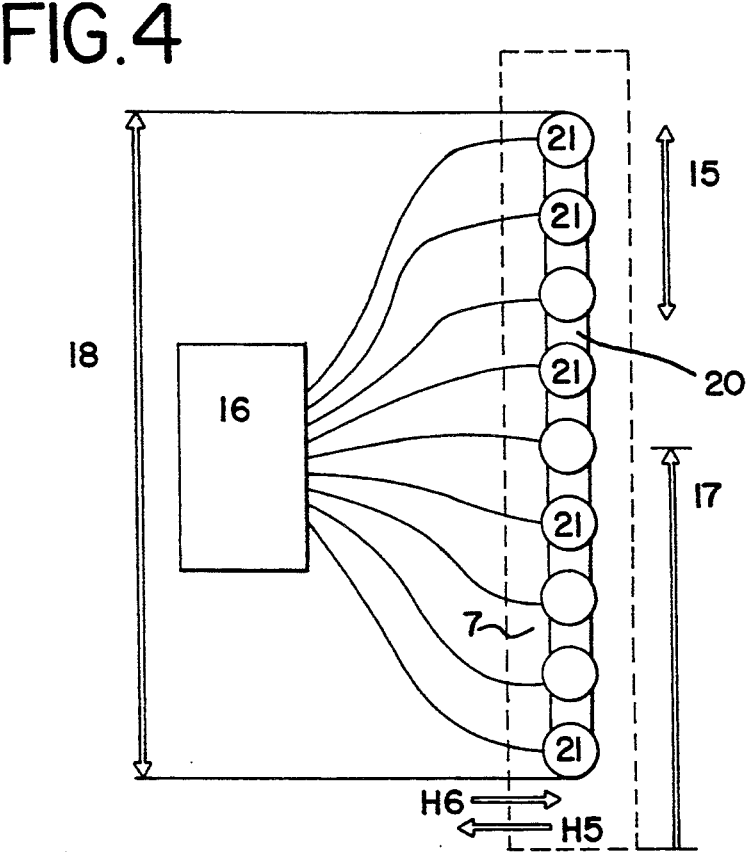
FIG. 4 depicts one more embodiment of the apparatus for implementing the method of the invention.

In the embodiments described above, the correct height 17 for the detector or detectors is obtained specifically by transferring the detector 1 upwards in direction V1 or downwards in direction V2. Another possibility of causing the detection or measurement to take place at a predetermined height, or at a height determined on the basis of measurement, is to use a detector arrangement 20 made up of a number of detectors 21, as shown in FIG. 4. In this arrangement, the detectors are preferably positioned successively in a row, and the length 18 of the arrangement has been arranged to be parallel with the vertical direction 15 of the cone of rays 7. In this case the measuring for the determination of the exposure value can be caused to take place by connecting, for example by means of an electronic control device 16, a certain desired detector 21, or several certain desired detectors, to carry out the detection itself. In other words, during the measurement the detectors 21 are all in the cone of rays 7, but, for the detection, one or a number of the detectors which is/are at the desired height or at the desired heights 17 is/are selected to function by activating it or them. By using the same detector arrangement 20 it is also possible to carry out the initial detection, or any stages of detection if there are several, by activating the detectors 21 which are at the desired height. Since in this case the detectors would remain in place in the cone of rays, at least when conventional detectors 21 are used, the detector arrangement must be transferred in the horizontal direction H5 out of the area of the cone of rays after the detection. For the subsequent detection the arrangement 20 will be returned in direction H6 into the area of the cone of rays.

We claim:

1. A method for imaging a desired object by using a panoramic x-ray radiography apparatus equipped with exposure automatics, the apparatus including an x-ray generator, an x-ray tube emitting a cone of rays, and an image receptor with its holder as well as at least one radiation dose measuring detector for detecting the cone of rays on that side of said receptor which is directed towards the x-ray tube, characterized in that the detecting of the cone of rays which has passed through the object, for the determination of the exposure value, is carried out during imaging at least at one predetermined point of several points positioned at different heights in the cone of rays and that said detection is performed at a moment when the cone of rays strikes the object to be examined or a corresponding object, which is determined on the basis of the distance of travel of the image receptor.

2. A method as set forth in claim 1 in which detection is performed based on a portion of the imaging distance.

3. A method as set forth in claim 1, in which the detection is performed at a preset initial detection.

4. A method according to claim 1 characterized in that the measuring detector is positioned vertically before the starting of the imaging at a predetermined height in relation to the image field, and that the detector or detectors can be positioned in a horizontal direction in relation to the cone of rays which has passed through the object.

5. A method according to claim 1 characterized in that the detector measuring at a given time is during the detection which determines the exposure value, or activated in a cone of rays at a predetermined velocity upward and/or downward and when appropriate be transferred automatically from the cone of rays after this detection.

6. A method according to claims 1 or 4 characterized in that the detecting which determines the exposure value starts and ends at predetermined points of the path of travel of the image receptor.

7. A method according to claims 1 or 4 characterized in that the detecting which determines the exposure value starts and ends at corresponding points of the imaging sequence.

8. A method according to claims 1 or 4 characterized in that the detecting which determines the exposure value starts and ends at radiation dose change of a predetermined magnitude initially detected.

9. A method according to claim 1 characterized in that the determination of the exposure level is implemented in two stages, of which the first, rougher stage is carried out either by manual control before the beginning of the imaging and/or immediately at the beginning of the imaging by the initial detection of the cone of rays in the area of the patient's neck, and the second, more precise stage, is carried out by a detection which starts when a cone of rays strikes the object to be examined or a corresponding object.

10. A method according to claim 9 in which the second more precise stage is carried out by detection which is determined on the basis of the distance of travel of the image receptor.

11. A method according to claim 1 in which the second more precise stage is carried out by detection which starts when the cone of rays strikes the object to be examined or corresponding object is determined by an initial detection setting.

12. A method according to claim 1 characterized in that on the basis of the intensity value of the detected radiation, primarily the current of the x-ray tube or the exposure time is adjusted and secondarily the voltage of the tube is adjusted in order to produce the correct exposure.

13. A method according to claim 1 characterized in that the said detection of the cone of rays for the determination of the exposure value is carried out by using a detector arrangement made up of a number of successive detectors in the vertical direction of the cone of rays in which case for each detection or each detection stage the detector detects at a height predetermined in each case in the image field is turned on by means of an electronic control device.

14. A method according to claims 9, 10, or 11 in that the said rougher determination of the exposure level is implemented by means of a separate, second detector which can be transferred relative to the cone of rays which has passed through the object.

15. A method according to claims 9, 10, or 11 in that the said rougher determination of the exposure level is implemented by means of a separate, second detector which can be transferred relative to the cone of rays by another detector of the detector arrangement.

16. A method according to claim 13 characterized in that the detector arrangement can be transferred in a horizontal direction into and out of the cone of rays.

* * * * *